US012342985B2

(12) United States Patent
McCabe

(10) Patent No.: US 12,342,985 B2
(45) Date of Patent: Jul. 1, 2025

(54) ENDOSCOPE END PROTECTOR

(71) Applicant: GA HEALTH COMPANY LIMITED, Shatin (HK)

(72) Inventor: Kenneth McCabe, Shatin (HK)

(73) Assignee: GA HEALTH COMPANY LIMITED, Shek Mun (HK)

( * ) Notice: Subject to any disclaimer, the term of this patent is extended or adjusted under 35 U.S.C. 154(b) by 771 days.

(21) Appl. No.: 16/895,394

(22) Filed: Jun. 8, 2020

(65) Prior Publication Data
US 2021/0378492 A1 Dec. 9, 2021

(51) Int. Cl.
*A61B 1/00* (2006.01)
*A61B 1/12* (2006.01)

(52) U.S. Cl.
CPC ...... *A61B 1/00137* (2013.01); *A61B 1/00089* (2013.01); *A61B 1/122* (2013.01)

(58) Field of Classification Search
CPC . A61B 1/00137; A61B 1/00089; A61B 1/122; A61B 1/0676; A61B 2017/00296
USPC ................................................. 600/121, 125
See application file for complete search history.

(56) References Cited

U.S. PATENT DOCUMENTS 10,182,705 B2 * 1/2019 Ramsey ............. A61B 1/00103
10,856,725 B2 * 12/2020 Wassenburg ........... B65D 85/54
11,696,674 B2 * 7/2023 Thornton ........... A61B 1/00137
600/127
2014/0343361 A1 * 11/2014 Salman ................ A61B 1/0615
600/125
2015/0069728 A1 * 3/2015 Seitz, III ............... A61M 25/00
206/305
2020/0015662 A1 * 1/2020 Kaye ................... A61B 1/00131

FOREIGN PATENT DOCUMENTS

JP H0515901 U 3/1993
WO WO20210249914 A1 12/2021

OTHER PUBLICATIONS

"Olympus launches Scope Pro-tech endoscopic tip protector" by Staff Writer on NS Medical Devices, May 21, 2019, hereinafter Scope Pro-tech. (Year: 2019).*
"Olympus launches Scope Pro-tech endoscopic tip protector" by Staff Writer on NS Medical Devices, May 21, 2019 (Year: 2019).*
PCT International Search Report and Written Opinion from corresponding International Application No. PCT/EP2021/065123, dated Sep. 6, 2021.
https://www.meditechendoscopy.com/products/scope-protech/; Sep. 2024.

* cited by examiner

*Primary Examiner* — Aaron B Fairchild
*Assistant Examiner* — Megan Elizabeth Monahan
(74) *Attorney, Agent, or Firm* — Hoffmann & Baron, LLP

(57) ABSTRACT

An endoscope distal end protector and method including a body having a plurality of interconnected spaced members forming a body interior. The body has a longitudinal axis and defines a plurality of openings into the body interior. A first cover is disposed on the body and includes a first aperture formed therein. The first aperture is deformable and adapted to permit an endoscope distal end to pass therethrough and into the body interior and adapted to resiliently engage the endoscope distal end to retain the body on the endoscope distal end.

23 Claims, 7 Drawing Sheets

ENDOSCOPE END PROTECTOR

TECHNICAL FIELD

The present disclosure relates to an apparatus and method for protecting medical endoscopes against damage during storage, transport, handling, cleaning, disinfection, and sterilization procedures.

BACKGROUND

The distal ends or tips of surgical endoscopes are typically somewhat bendable cylindrical members circumferentially bound by a fluid-impervious polymeric wrapping and containing electronic chips and other delicate components. It is not uncommon for the polymeric wrapping to be punctured or ripped when carelessly handled during storage or removal from storage, or while being disinfected between surgical procedures. Specifically, the endoscope assembly is somewhat unwieldy to handle, and the distal end is often dropped onto a floor or other hard surface, sometimes being inadvertently kicked or stepped on. The unwieldiness of the assembly can also result in the distal end impacting against a table, cabinet or other fixture while the assembly is being handled or carried from one location to another. In addition to the potential for rupture and puncture of the polymeric wrapping, the impact of the head against a hard surface can cause damage to the interior components of the head, particularly sensitive optical components and integrated circuit chips of an endoscope camera. Puncture or rupture of the polymeric wrapping, if undetected, results in reprocessing liquids or patient effluent solutions entering the endoscope tip and damaging the components.

In addition, the tip of the endoscopes may roll when it is laying on a flat surface such as the top tray of an endoscopy cart. Sometimes when the endoscope is in this location, instruments, such as biopsy forceps may also be placed on the same tray. Some of these forceps contain needles and the needles sometime puncture the flexible section of the endoscope know as the A rubber.

Therefore, it is desirable to provide an end protector for an endoscope that is easy to put on and remove and protects the end of the endoscope and also does not interfere with the cleaning, disinfection and sanitization process of the endoscope.

SUMMARY

The present disclosure provides an endoscope distal end protector which includes a body including a plurality of interconnected spaced members forming a body interior. The body has a longitudinal axis and defines a plurality of openings into the body interior. A first cover is disposed on the body and includes a first aperture formed therein. The first aperture is deformable and adapted to permit an endoscope distal end to pass therethrough and into the body interior and adapted to resiliently engage the endo scope distal end to retain the body on the endoscope distal end.

The present disclosure also includes a second cover disposed on the body and spaced from the first cover a distance along the longitudinal axis of the body. The second cover includes a second aperture formed therein which is deformable to permit an endoscope distal end to pass therethrough.

The present disclosure further provides an endoscope distal end protector including a body having a plurality of interconnected spaced members forming a body interior. The body has a longitudinal axis. The body defines a plurality of openings into the body interior. The plurality of interconnected members include a plurality of spaced concentric rings. At least one of the plurality of rings has an outer perimeter including a flat edge. A first resilient cover is disposed on a first of the plurality of rings and includes a first aperture formed therein. The first aperture is deformable and adapted to permit an endoscope distal end to pass therethrough and into the body interior and adapted to resiliently engage the endoscope distal end to retain the body on the endoscope distal end. A second resilient cover is disposed on a second of the plurality of rings and spaced from the first cover a distance along the longitudinal axis of the body. The second cover includes a second aperture formed therein and being deformable to permit an endoscope distal end to pass therethrough.

The present disclosure further provides a method of protecting a distal end of an endoscope including obtaining an endoscope distal end protector including a body including a plurality of interconnected spaced members forming a body interior. The body has a longitudinal axis. The body defines a plurality of openings into the body interior. A first cover is disposed on the body and includes a first aperture formed therein. The first aperture is deformable and adapted to permit an endoscope distal end to pass therethrough and into the body interior, and adapted to resiliently engage the endoscope distal end and retain the body on the endoscope distal end. The method further includes inserting a distal end of an endoscope though the first aperture and into the body interior and through the second aperture wherein the first cover resiliently engages the distal end of the endoscope and the protector is removably retained on the endoscope.

DETAILED DESCRIPTION

The present disclosure is directed to a device for protecting the distal end or tip of an endoscope or similar instrument. Similar instruments may include, for example, any instrument having an elongate shaft and a distal tip where it would be desirable or beneficial to protect the tip from damage. Typically these instruments will be optical instruments having a lens or part of a lens system at the distal end. Such instruments may be, but are not limited to, borescopes such as those used in industrial applications or endoscopes such as those used in medical applications. Endoscopes may include scopes such as surgical laproscopes, colonoscopes, gastroscopes, esophagoscopes and sigmoidoscopes. It will be understood that references in the following description to an endoscope also encompasses surgical laproscopes, borescopes and similar instruments.

Figure 1:
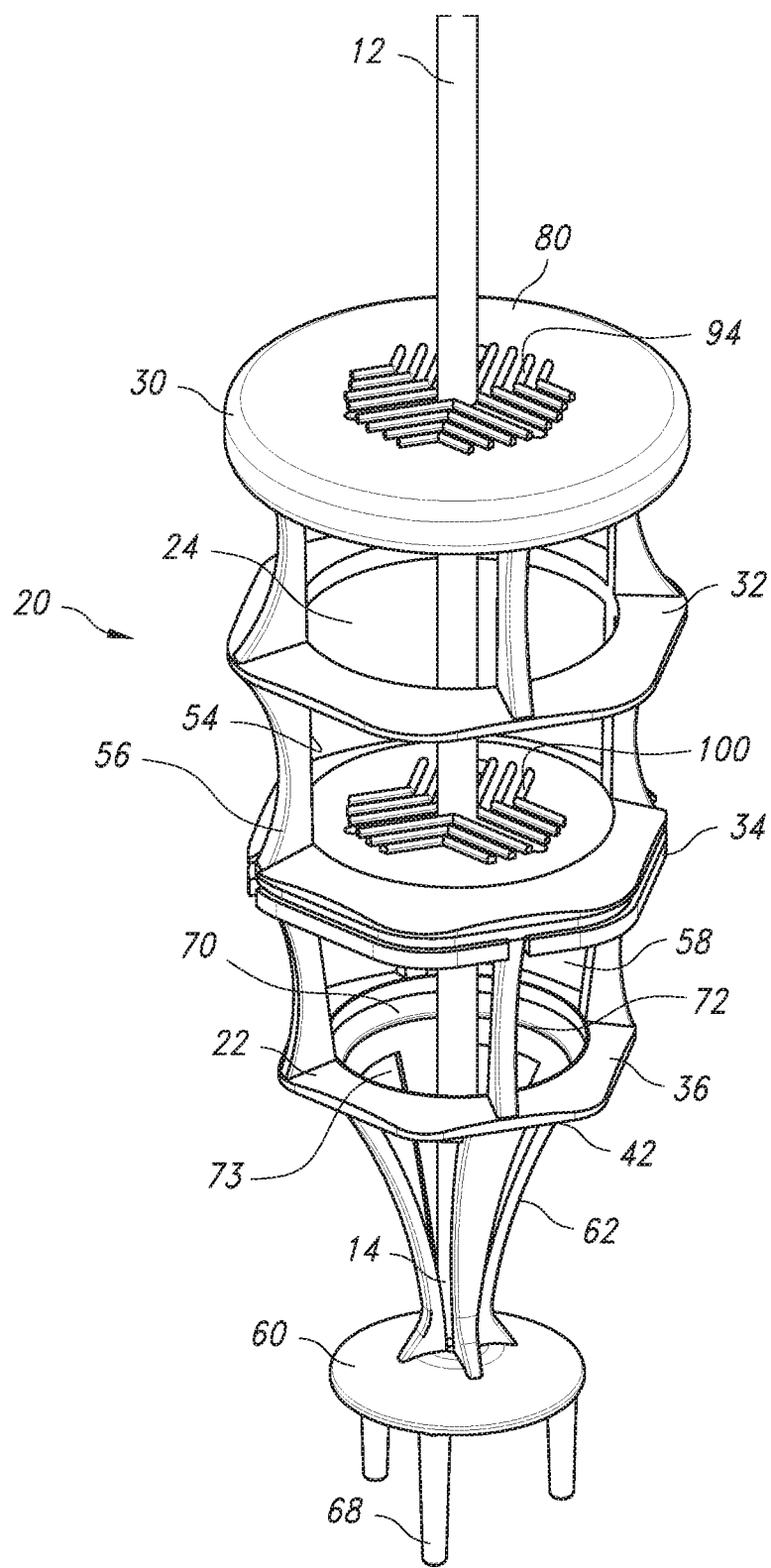
FIG. 1 is a perspective view of an endoscope end protector having a narrow endoscope insertion tube inserted therein.
Figure 2:
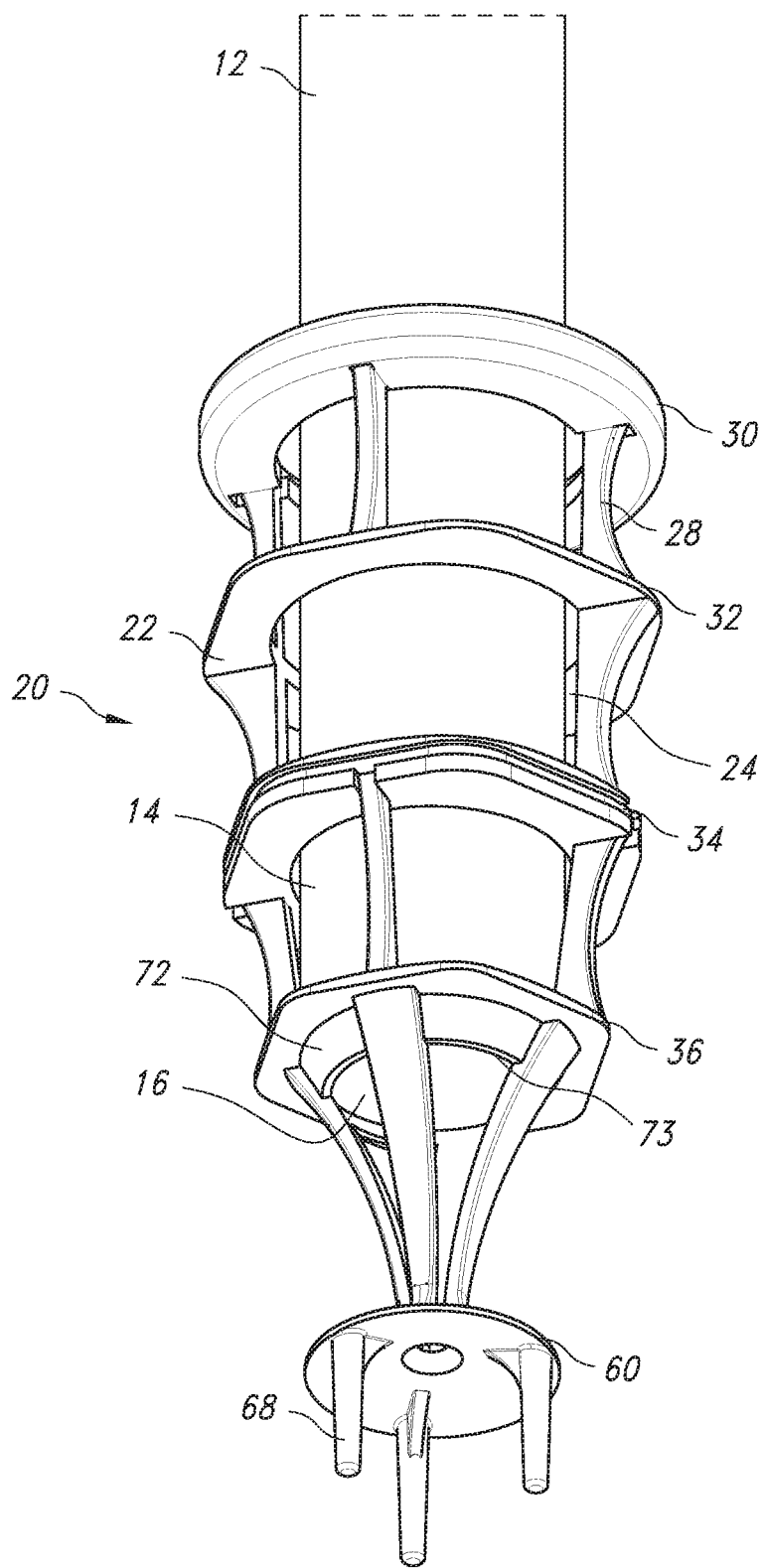
FIG. 2 is a perspective view of an endoscope end protector having a wide endoscope insertion tube inserted therein.
Figure 3:
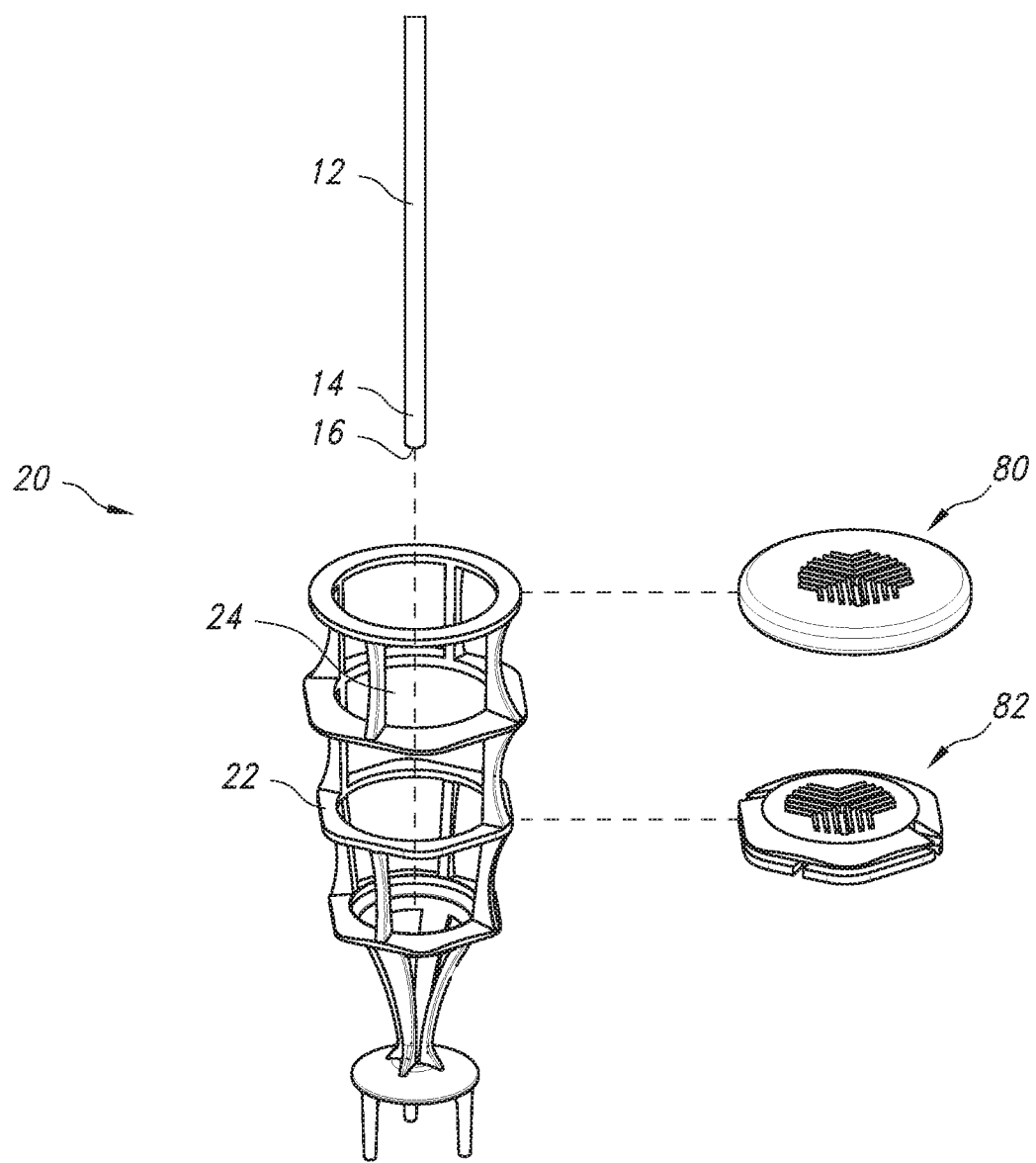
FIG. 3 is an exploded view of an endoscope end protector.
Figure 4:
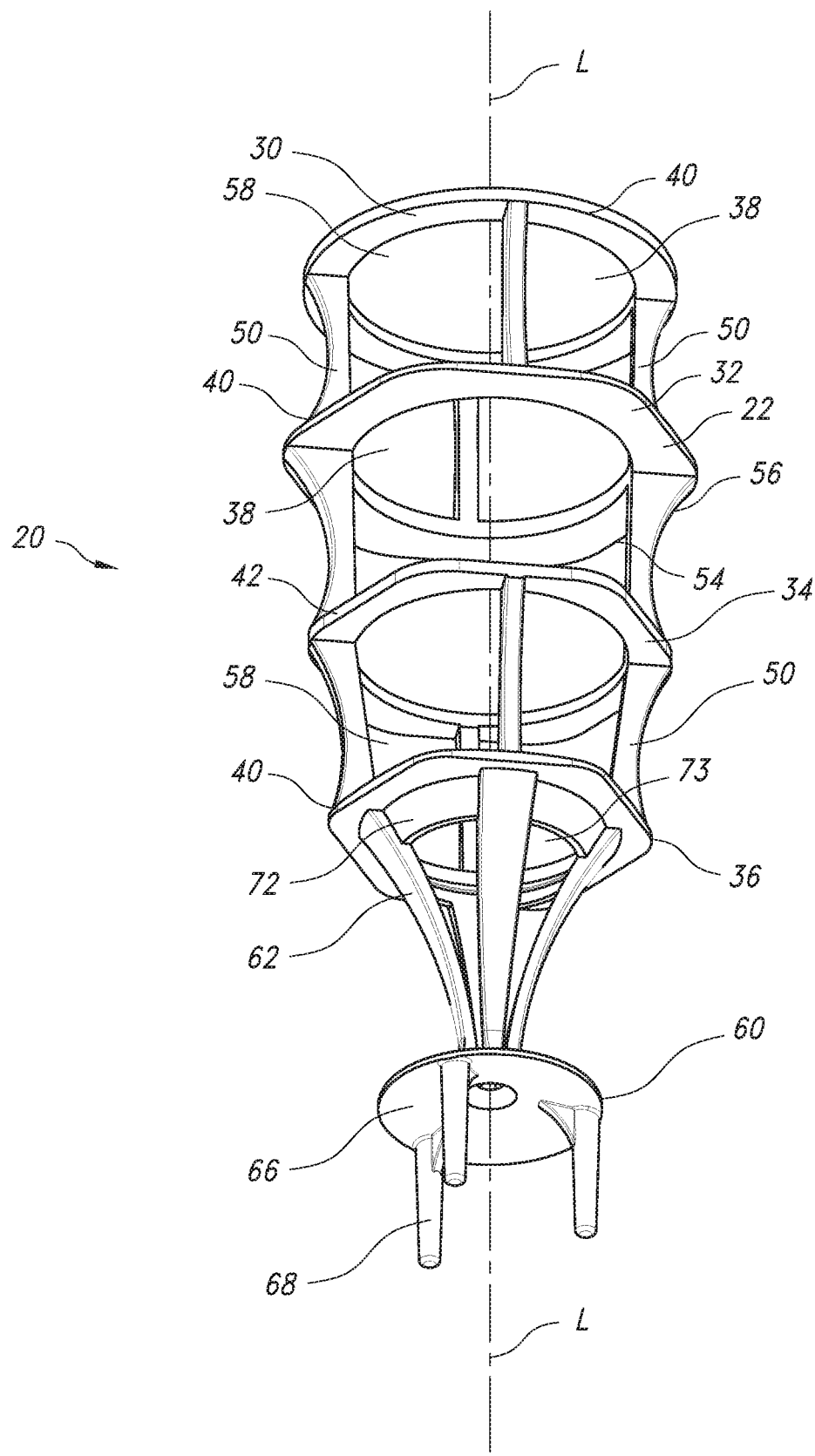
FIG. 4 is a perspective view of an endoscope end protector body.

With reference to FIGS. 1-2, an endoscope elongate shaft or insertion tube 12 having a distal end or tip 14 is shown. The insertion tube 12 may be flexible or rigid, depending on the specific application. Typically the distal tip 14 of the endoscope shaft 12 will include an end face 16 that is planar and is substantially perpendicular to a longitudinal axis of the shaft 12. However, in some endoscopes the end face may be curved, or the tip may be tapered such that the end face is at an angle of less than 90 degrees to the longitudinal axis.

With reference to FIGS. 1 to 5, a tip protector device 20 is configured to engage with and attach to the endoscope distal tip 14 to protect the tip 14 and, in particular, to protect the tip and its end face 16 from potential damage. The protector device 20 includes a cage-like body 22 including a plurality of interconnected members 23 to form a body interior 24 in which the tip 14 is received. With specific reference to FIGS. 4 and 5, the interconnected members 23 may be formed of a rigid plastic, for example polyethylene, and include a plurality of concentric rings 28, namely a first ring 30, second ring 32, third ring 34 and fourth ring 36. It is contemplated that the number of rings could be more or less. Each of the plurality of rings 28 is spaced a distance from each other along a longitudinal axis L-L of the protector. Each ring 28 has a central aperture 38, which provides an opening for the endoscope distal tip 14 to extend.

The rings 28 may each have an outer periphery 40. The outer periphery 40 of one or more of the rings 28 may have at least one flat edge 42. For example, the first ring 30 may have a round periphery and the outer periphery of the second, third, and fourth rings 32, 34, 36 may have a non-round shape. For the non-round rings, the outer periphery 40 can be formed of a plurality of interconnecting flat edges 42. In one embodiment, the outer periphery is a hexagon, however, it is contemplated that the outer periphery could be a number of round and non-round different shapes. The flat edges 42 resist rolling such that when the protector device 20 is placed on an endoscope, the protector 20 will help prevent the endoscope from inadvertently rolling off a surface. The rings 28 may have different outer diameters. For example, the second ring 32 may have the largest diameter, with the third and fourth rings 34, 36 being progressively smaller. When placed on the surface the non-round second ring 32 will contact the surface and resist rolling.

Figure 5:
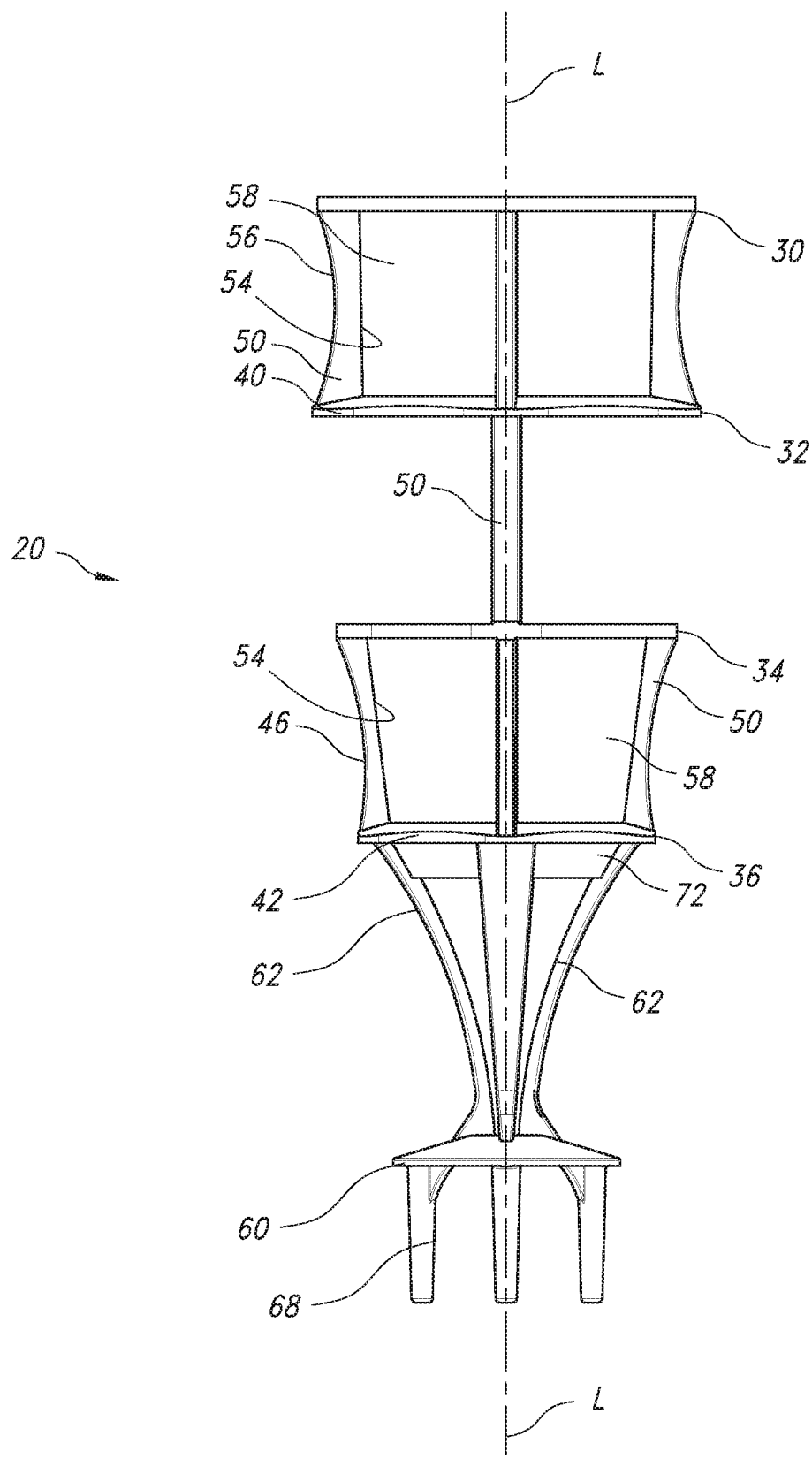
FIG. 5 is a side elevational view of the endoscope tip protector body.

The interconnected members 23 forming body 22 may include a plurality of spacers 50 which separate the rings 28 from each other in the longitudinal direction. Each spacer 50 extends between adjacent rings. Adjacent rings are connected by at least two spacers, although in the embodiment shown four spacers between each set of adjacent rings are included. For example four spacers may separate the first ring 30 from the second ring 32 and the third ring 34 from the fourth ring 36. Two spacers 50 may separate the second ring 32 from the third ring 34 as shown in FIG. 5. The spacers 50 may have a generally straight inner elongate surface 54 facing the interior. On the opposite side, the spacers have a concave surface 56. The space between the spacers creates a plurality of openings 58 that permit air to pass through. Therefore, if an endoscope has been reprocessed and is covered with cleaning, disinfecting and/or sterilization solutions, the openings permit air to flow over the distal tip 14 to enhance drying.

The interconnected members 23 may include a plurality of radially spaced supports 62 which operably connect the fourth ring 36 to a base 60. The base 60 supports are tapered inwardly such that the space 64 between them narrows as they extend from the fourth ring 36 to the base 60. At the surface of the base 60, the base supports are spaced to accommodate endoscopes tubes having a relatively narrow distal tip diameter, e.g., 2.5 mm. The tapered space 64 formed by the supports 62 permits the protector 20 to accommodate distal tips 14 of a variety of different diameters. Therefore, there is no need for having a number of different protectors to accommodate different size endoscopes. When the endoscope distal tip 14 is fully inserted into the protector, the base supports 62 engage the tip and space the end face 16 from the base. The larger the diameter of the distal tip 14 the further way from the end face 16 will be from the base 60 due to the tapered nature of the supports 62. The space permits air to flow between the end face 16 and the protector to enhance thorough drying and also to further protect the sensitive end face 16 from damage. The base 60 also includes a planar surface 66 having a plurality of legs 68 projecting outwardly therefrom. The legs 68 help to space the end of the protector device from a surface to provide extra protection to the endoscope distal tip 14.

With reference to FIG. 2, the distal tip 14 of wider endoscopes, e.g., 14 mm, are supported in a seat 70 formed on the fourth ring 36. The seat 70 includes an annular flange 72 defining an opening 73. The flange 72 extends radially inwardly from the fourth ring. The flange 72 forms a shallow frustoconical structure that supports the end face 16 as shown in FIG. 2. When in the seat, the opening 73 permits air to flow between the end face 16 and the protector to enhance thorough drying and also to further protect the sensitive end face 16 from damage.

It is contemplated that the body 22, interconnected members 23, rings 28, supports 62, base 60 and legs 68 are all integrally formed as one piece. The body 22 may be made of a material that retains its shape such as polypropylene.

With reference to FIGS. 6A-B and 7A-B, the protector 20 further includes an outer cover 80 and inner cover 82 disposed on two of the rings 28. It is contemplated that the shape of the inner and outer cover may be formed to correspond to the configuration of the rings to which they are secured. The inner and outer covers 80, 82 help to removable secure the protector 20 to the distal end 14. The outer cover 80 is a resilient member formed of an elastomeric material, such as silicone rubber, which is disposed on the first ring 30. The elasticity of the outer cover 80 permits it to be stretched over the first ring 30 and secured thereto. The outer cover 80 includes a central surface 84 having a perimeter rim 86. Extending between the central surface 84 from the rim is a radially inwardly extending flange 88 spaced from the central surface. A space between the flange 88 and the central surface 84 accommodates the first ring 30. The flange 88 includes a plurality of slots 90 to accommodate the spacers 50 connecting the first ring 30 to the second ring 32. While the use of two covers is shown and described herein, it is within the contemplation of the present disclosure that a single cover could be used or more that two covers could be employed.

Figure 6A:
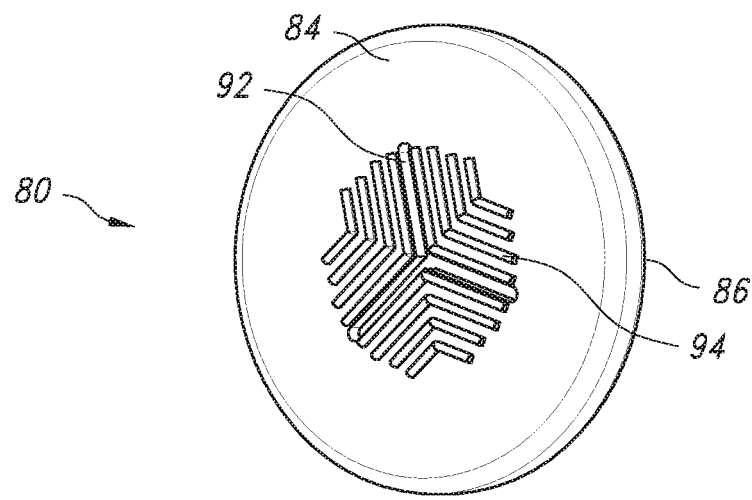
FIG. 6A is a top perspective view of an outer cover.
Figure 6B:
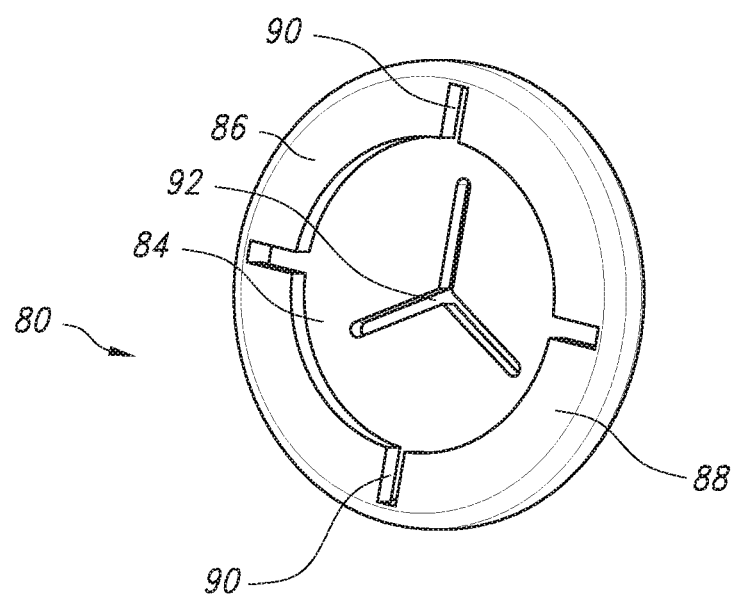
FIG. 6B is a bottom perspective view of an outer cover.

With specific reference to FIGS. 6A and 6B, the central surface 84 may include an aperture 92 therein to permit the distal tip 14 of the insertion tube 12 to pass there through. The aperture 92 may be in the form of a narrow slit having a Y-shaped configuration as shown in FIG. 6B. However, it is contemplated that the aperture could be of a variety of configurations. For example, the aperture could be, for example, in the form of a flap, star design, prongs, bumps and/or nubs having different thicknesses. The aperture 92 may be sized to accommodate a wide range of endoscope insertion tube diameters. When the distal tip 14 is inserted through the aperture, the resilient nature of the outer cover causes the aperture 92 to enlarge to permit the distal tip to pass through. The outer cover material surrounding the distal tip 14 elastically urges against the tip and help to secure the protector 20 to the distal tip 14. Adjacent the aperture 92 is a plurality of raised ridges or blades forming a set of wipers 94 as shown in FIG. 6A. It is contemplated that the wipers 94 may be in the form of linear or curved structures, or combinations of both, surrounding or partially surrounding the aperture 92. As the distal tip 14 is inserted into the aperture 92, the central portion deforms and causes the wipers 94 to engage the distal tip 14. This results in excess cleaning/disinfecting solution to be wiped off the distal tip. The set of wipers 94 may radiate out from the aperture 92 and diminish in length the further they are from the aperture.

Figure 7A:
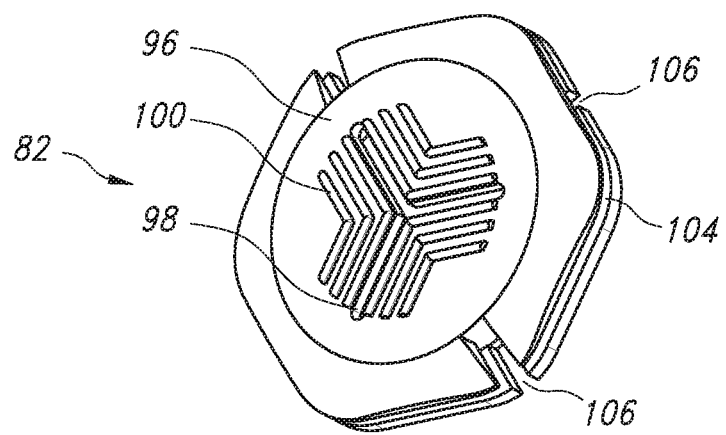
FIG. 7A is a top perspective view of an inner cover.
Figure 7B:
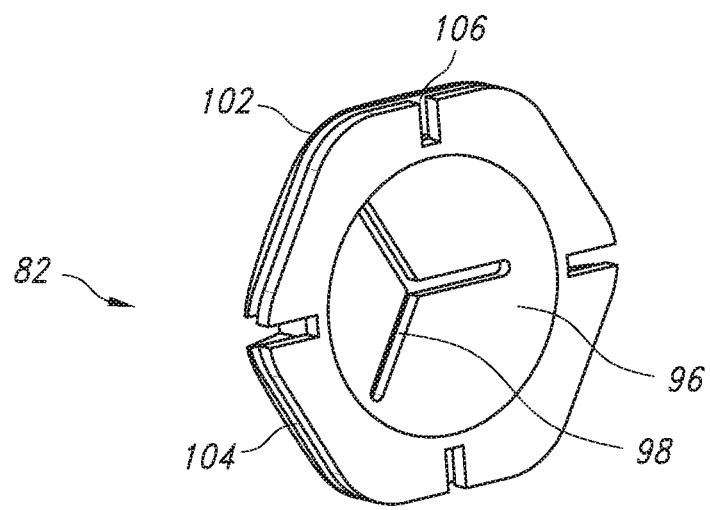
FIG. 7B is a bottom perspective view of an inner cover.

With reference to FIGS. 7A and 7B, the inner cover 82 may be disposed on the third ring 34. The inner cover 82 may be formed of an elastomeric material similar to that that of the outer cover 80, for example, silicone rubber. The inner cover 82 may have a central surface 96 similar to that of the outer cover 80. The central surface 96 may include an aperture 98 in the form of a slit as shown in FIG. 7B. A plurality of raised ridged or blades forming a set of wipers 100 is disposed around the aperture 98. The inner cover 82 is bounded by a rim 102 having a perimeter channel 104 for receiving the third ring 34 within. The inner cover may have a pair of opposed slots 106 to receive the spacers 50. The resilient nature of the inner cover retains it on the third ring 34. The inner cover material surrounding the distal tip 14 elastically urges against the distal tip and help to secure the protector 20 to the distal tip 14. As the distal tip 14 is inserted into the aperture 98, the central portion deforms and causes the wipers 100 to engage the distal tip 14. This results in excess cleaning/disinfecting solution to be wiped off the distal tip. The set of wipers 100 may radiate out from the aperture 92 and diminish in length the further they are from the aperture.

In use, an endoscope would typically be cleaned, disinfected, and/or sterilized after being used in a procedure. The distal tip 14 of the endoscope tube 12 may then be aligned with longitudinal axis of the protector L-L and inserted through the outer cover aperture 92. Thus, the outer cover 80 is deformed the aperture 92 increases in size and the set of wipers 94 engage the distal tip 14. This wipes away excess moisture. The distal tip 14 is further slid into the body interior 24 until it engages the inner cover 82 and deforms the aperture 98 therein. The aperture 98 expands as the distal tip 14 slides therethrough. The set of wipers 100 on the inner cover further wipe away remaining moister on the distal tip 14. The distal tip 14 is further advanced into the body interior 24. If the tube 12 is narrower than the opening formed by the flange 72, the distal tip will continue to be advanced until the tube 12 enters the tapered space 64 and engages the tapered supports 62. Further advancement of the distal tip 14 is then prevented by this engagement. In this position, the distal tip is engaged by the supports 62 at a plurality of radially spaced locations. If the tube 12 is wider than the opening formed by the flange 72, it will engage the seat 70 and come to rest in that position. With the tip protector secured to the distal tip 14, the tip is protected. In addition, the plurality of openings 58 existing in the cage-like body 22 permits air to flow over the distal tip allowing it to dry and avoid trapping moisture. When the endoscope is ready to be used for another procedure, the protector 20 may be removed by pulling the protector 20 off of the endoscope tube 12 such that the elastic engagement between the tube 12 and the inner and outer cover is overcome and the protector slides off of the endoscope tube 12.

Given the teachings provided herein, one of ordinary skill in the art will be able to contemplate other implementations and applications of the techniques and disclosed embodiments. Although illustrative embodiments have been described herein with reference to the accompanying drawings, it is to be understood that illustrative embodiments are not limited to those precise embodiments, and that various other changes and modifications are made therein by one skilled in the art without departing from the scope of the appended claims.

What is claimed is:

1. An endoscope distal end protector comprising:
a body including a plurality of interconnected spaced members forming a body interior, the interconnected spaced members including a plurality of rings and a plurality of spacers, and the plurality of rings being separated from each other a distance along a longitudinal axis of the body by the plurality of spacers, and the body defining a plurality of openings into the body interior;
a base is operably connected to one of the plurality of rings by a plurality of supports, and wherein the plurality of supports are tapered inwardly toward the longitudinal axis of the body and wherein a space defined between the plurality of supports extends along the longitudinal axis of the body for receiving an endoscope distal end there through and the space narrows as the plurality of supports extends from the one of the plurality of rings to the base, the plurality of supports each having an inner surface forming a distal end abutment surface for abutting the endoscope distal end and spacing the endoscope distal end from the base; and
a first cover disposed on the body, and including a first aperture formed therein, the first aperture being deformable and adapted to permit the endoscope distal end to pass therethrough and into the body interior, and adapted to resiliently engage the endoscope distal end to retain the body on the endoscope distal end.

2. The protector as defined in claim 1, wherein a second cover is disposed on the body and spaced from the first cover a distance along the longitudinal axis of the body, the second cover including a second aperture formed therein and being deformable to permit the endoscope distal end to pass therethrough.

3. The protector as defined in claim 1, wherein one of the plurality of rings forms a first ring and the first ring forms a first end of the body and the first cover is disposed on the first ring.

4. The protector as defined in claim 3, wherein the second cover is disposed on a second of the plurality of rings.

5. The protector as defined in claim 2, wherein the first aperture and second aperture are aligned along the longitudinal axis of the body.

6. The protector as defined in claim 1, wherein the first cover has a plurality of raised linear blades, each having a length greater that its width, forming first wipers disposed adjacent the first aperture, the first wipers adapted to engage the endoscope distal end when inserted through the first aperture and to remove moisture therefrom.

7. The protector as defined in claim 2, wherein the second cover has a plurality of raised linear blades, each having a length greater that its width, forming second wipers disposed adjacent the second aperture, the second wipers adapted to engage the endoscope distal end when inserted through the second aperture and to remove moisture therefrom.

8. The protector as defined in claim 1, wherein the plurality of rings includes a first and second rings and a third ring disposed between the first and second rings, the third ring having a perimeter edge formed of a plurality of interconnecting non-round edges.

9. The protector as defined in claim 8, wherein the plurality of rings includes a fourth ring operatively connected to the second ring, and the base is operably connected to the fourth ring by the plurality of supports.

10. The protector as defined in claim 9, wherein the base is located along the longitudinal axis of the body.

11. The protector as defined in claim 1, wherein the first cover has a resilient planar surface extending over an opening in the first ring, an aperture being disposed on the resilient planar surface.

12. The protector as defined in claim 9, wherein the fourth ring includes a radially inwardly extending flange forming a seat adapted to support the endoscope distal end.

13. An endoscope distal end protector comprising:
a body including a plurality of interconnected spaced members forming a body interior, the body having a longitudinal axis, the body is bounded on a one end by a base, the base having a bottom surface and a plurality of spaced legs extending outwardly from the bottom surface in an axial direction along the longitudinal axis of the body and away from the body interior, the body defining a plurality of openings into the body interior, the plurality of interconnected spaced members including a plurality of spaced concentric rings, wherein at least one of the plurality of spaced concentric rings has an outer perimeter including a flat edge;
a first resilient cover disposed on a first of the plurality of spaced concentric rings and including a first aperture formed therein, the first aperture being deformable and adapted to permit an endoscope distal end to pass therethrough and into the body interior and adapted to resiliently engage the endoscope distal end to retain the body on the endoscope distal end; and
a second resilient cover disposed on a second of the plurality of rings and spaced from the first cover a distance along the longitudinal axis of the body, the second resilient cover including a second aperture formed therein and being deformable to permit the endoscope distal end to pass therethrough.

14. The protector as defined in claim 13, wherein the first aperture and second aperture are aligned along the longitudinal axis of the body.

15. The protector as defined in claim 13, wherein the first cover has a plurality of raised ridges forming first wipers disposed adjacent the first aperture, the first wipers adapted to engage the endoscope distal end when inserted through the first aperture.

16. The protector as defined in claim 15, wherein the second resilient cover has a plurality of raised ridges forming second wipers disposed adjacent the second aperture, the second wipers adapted to engage the endoscope distal end when inserted through the second aperture.

17. The protector as defined in claim 13, wherein at least one of the plurality of rings has a perimeter edge formed of a plurality of interconnecting non-round edges.

18. The protector as defined in claim 1, wherein the base has a tapered upper surface leading away from the longitudinal axis of the body to direct fluid away from the longitudinal axis of the body, and the base having a through hole therein adapted to permit fluid to flow there though from the body interior.

19. The protector as defined in claim 1, wherein one of the plurality of rings includes a radially inwardly extending flange forming a seat adapted to support an end face of the endoscope distal end, the seat being axially spaced from the distal end engagement surface.

20. The protector as defined in claim 13, wherein the base has a tapered upper surface leading away from the longitudinal axis of the body and away from the plurality of supports to direct fluid away from the longitudinal axis of the body, and the tapered upper surface having a through hole therein adapted to permit fluid to flow there though from the body interior, and the base has a lower surface opposed from the tapered upper surface and the plurality of spaced legs extending outwardly from the lower surface.

21. The protector as defined in claim 1, wherein the plurality of supports each have a radial outer surface that taper radially inwardly as the plurality of supports extend toward the base.

22. The protector as defined in claim 1, wherein the plurality of supports each have a convex inner surface that tapers inwardly toward the longitudinal axis of the body.

23. The protector as defined in claim 13, wherein the base is operably connected to one of the plurality of rings by a plurality of supports, and wherein the plurality of supports are tapered inwardly toward the longitudinal axis of the body and wherein a space defined between the plurality of supports extends along the longitudinal axis of the body for receiving an endoscope distal end there through and the space narrows as the plurality of supports extends from the one of the plurality of rings to the base, the plurality of supports each having an inner surface forming a distal end abutment surface for abutting the endoscope distal end and spacing the endoscope distal end from the base.

* * * * *